United States Patent [19]

Yamazaki et al.

[11] Patent Number: 5,292,663

[45] Date of Patent: Mar. 8, 1994

[54] METHOD OF TREATING BLOOD CONTAINING LABILE GLYCOSYLATED HEMOGLOBIN $A_{1C}$

[75] Inventors: Kazutoshi Yamazaki, Ohtsu; Masahiro Takechi, Nishinomiya; Toshiki Kawabe, Kyoto; Masayuki Yokoi, Kusatsu, all of Japan

[73] Assignee: Sekisui Kagaku Kogyo Kabushiki Kaisha, Osaka, Japan

[21] Appl. No.: 56,989

[22] Filed: May 3, 1993

Related U.S. Application Data

[60] Division of Ser. No. 758,383, Sep. 3, 1991, abandoned, which is a continuation of Ser. No. 252,774, Oct. 3, 1988, abandoned.

[30] Foreign Application Priority Data

Nov. 30, 1987 [JP] Japan ................................ 62-303782
Dec. 22, 1987 [JP] Japan ................................ 62-326463

[51] Int. Cl.$^5$ .................... G01N 33/72; G01N 30/04
[52] U.S. Cl. ............................. 436/67; 436/15; 436/17; 436/18; 436/161; 436/175; 530/417
[58] Field of Search ............... 436/15, 17, 18, 67, 436/161, 175; 530/385, 417

[56] References Cited

U.S. PATENT DOCUMENTS

| | | |
|---|---|---|
| 3,689,633 | 9/1972 | Matsushima et al. ........... 436/814 X |
| 3,814,820 | 6/1974 | Busta et al. ...................... 426/268 X |
| 3,864,085 | 2/1975 | Woodbridge ..................... 436/164 X |
| 4,297,238 | 10/1981 | Vormbrock et al. .................. 436/17 |
| 4,399,227 | 8/1983 | Niederau et al. ...................... 436/67 |
| 4,409,335 | 10/1983 | Hanamoto et al. . |
| 4,414,305 | 11/1983 | Nakamura et al. ............. 430/469 X |
| 4,876,188 | 10/1989 | Smith et al. ..................... 436/67 X |
| 4,879,039 | 11/1989 | Takahashi et al. ............... 436/67 X |

FOREIGN PATENT DOCUMENTS 63-298064 12/1988 Japan .

OTHER PUBLICATIONS

Vandegrift et al, Chemical Abstracts; vol. 95, Abstract No. 95:5371t, 1981.
W. Pschyrembel, "Klinisches Wörterbuch", 254th edition, 1982, Walter de Gruyter, Berlin–New York, p. 446, entry titled Hämolyse (in vitro).
"Ullmanns Encyklopädie der technischen Chemie", 4th Edition, (1979) vol. 18, pp. 306–308.
D. E. Goldstein et al, *Clin. Chem.* (1986) 32:B64–B70.
Clinical Chemistry vol. 28, No. 3, 1982 pp. 512–515.
Chemical Abstracts, vol. 111, 23 Oct. 1989, p. 372, Abstract No. 150054v.

*Primary Examiner*—James C. Housel
*Assistant Examiner*—Jan M. Ludlow
*Attorney, Agent, or Firm*—Morrison & Foerster

[57] ABSTRACT

An eliminating agent used for the measurement of the amount of glycosylated hemoglobins in a blood sample is provided. The eliminating agent comprises condensed phosphoric acids and/or the salts thereof as the main ingredient, wherein the agent eliminates labile glycosylated hemoglobin $A_{1c}$ into non-glycosylated hemoglobin and glucose. There is also provided a reagent comprising the eliminating agent and a hemolysis agent, which is used for the measurement of the amount of glycosylated hemoglobins; and an eluent comprising the eliminating agent, which is used for the separation of glycosylated hemoglobins in blood samples by ion-exchange chromatography to measure the amount of the glycosylated hemoglobins. A method for measuring the amount of glycosylated hemoglobin $A_{1c}$ in a blood sample involves the use of the eliminating agent, the reagent comprising the eliminating agent and the hemolysis agent, and/or the eluent.

14 Claims, 2 Drawing Sheets

METHOD OF TREATING BLOOD CONTAINING LABILE GLYCOSYLATED HEMOGLOBIN A$_{1C}$

CROSS-REFERENCES

This application is a divisional application of earlier filed allowed U.S. application Ser. No. 07/758,383 filed Sep. 3, 1991, now abandoned, which is a continuation of earlier filed U.S. application Ser. No. 07/252,774 filed Oct. 3, 1988, now abandoned, which applications are incorporated herein by reference and to which applications we claim priority under 35 USC § 120. Further, the present application claims priority under 35 USC § 119 to Japanese applications 62-303782 filed Nov. 30, 1987 and 62-326463 filed Dec. 22, 1987.

This invention relates to an eliminating agent for labile glycosylated hemoglobin that is used for the measurement of glycosylated hemoglobins (hemoglobin A$_1$) in blood, and in particular, for the measurement of hemoglobin A$_{1c}$; and also relates to a method for the measurement of hemoglobin A$_{1c}$ in which the said agent is used. This invention relates also to a reagent for use in the measurement of glycosylated hemoglobins that contains the above eliminating agent and a hemolysis agent, and to an eluent for use in the measurement of glycosylated hemoglobins in the chromatography, which eluent contains the above eliminating agent and a buffer.

BACKGROUND OF THE INVENTION

One of the indices of medical treatment for diabetes mellitus that are known and currently being used is the amounts of glycosylated hemoglobins (i.e., hemoglobin A$_1$), and the amount of hemoglobin A$_{1c}$ in particular. As is shown below in equation 1, hemoglobin A$_{1c}$ is a complex in which one molecule of glucose is bound non-enzymatically to the N-terminal amino acid, valine, of the β-chain of hemoglobin (below, abbreviated Hb). When the glucose has been bound to the amino acid mentioned above, first, as shown below in the equation, labile HbA$_{1c}$ I, which is a Schiff base, is formed:

In the above equation 1, β-A—NH$_2$ represents Hb, and the NH$_2$ here shows the amino group in the N-terminal amino acid, valine, of the β-chain of the said Hb.

The reaction that produces this labile HbA$_{1c}$ I, is a reversible reaction, and depending on the glucose concentration, the equilibrium will tend to go either in the direction of the production of the labile HbA$_{1c}$ I, or else it will tend to go in the direction of its elimination. Compound I is converted irreversibly into the stable HbA$_{1c}$ II by the Amadori rearrangement.

HbA$_{1c}$ can be separated from other hemoglobins by means of high-performance liquid chromatography, and measured in terms of its optical density (OD), but it is not possible to separate the stable HbA$_{1c}$ (S-HbA$_{1c}$) and the labile HbA$_{1c}$ (L-HbA$_{1c}$) and to measure them separately. Therefore, it is not possible to obtain a reliable value of HbA$_{1c}$. The reason is that the amount of L-HbA$_{1c}$ varies depending on the concentration of glucose (that is, the blood glucose) that is present, and the concentration of glucose in the blood changes rapidly and greatly, depending on meals and physical activity.

To solve the problems described above, attempts to eliminate L-HbA$_{1c}$ from blood samples and to measure the amount of S-HbA$_{1c}$ have been made. For example, in a paper by David M. Nathan et al. (*Clinical Chemistry*, 28, 512–515, 1982), semicarbazide and aniline are used as agents to eliminate the L-HbA$_{1c}$, and it is disclosed that the blood sample is treated with these agents at 38° C. for 30 minutes. The semicarbazide captures the glucose, and acts as a nucleophilic reagent as well, competing with the amino group of the Hb. The aniline acts as a catalyst. The result is that virtually all of the L-HbA$_{1c}$ is eliminated. However, because the reaction for the elimination of L-HbA$_{1c}$ is at an acidic pH (pH 5.0) and at a relatively high temperature (38° C.) for a long period of time (30 minutes), some denaturation of the Hb (for example, elimination of the heme) may occur. For example, when the elution pattern for ion-exchange chromatography is examined, the height of the peak decreases owing to fading of color caused by the elimination of heme, and the peaks that correspond to HbA$_{1a}$ and HbA$_{1b}$ respectively are seen as being larger.

In Japanese Laid-Open Publication 58-210024, a dihydroxyboryl compound (i.e., a derivative of boric acid) that is as an agent for the elimination of L-HbA$_{1c}$ is disclosed. This dihydroxyboryl compound reacts with glucose to form a complex, the result of which is to cause the elimination of the L-HbA$_{1c}$. However, to eliminate the L-HbA$_{1c}$, high concentrations of the dihydroxyboryl compound are needed. For example, about 0.1–1.0 M of the said compound is needed for a sample that contains blood that has been hemolyzed. When the hemolyzed blood is put on the column with the use of an eluent that contains the said dihydroxyboryl compound, it is necessary to use the compound at the concentrations of 0.01–0.15 M in the eluent. When this kind of high concentration of dihydroxyboryl compound is used for the eluent for ion-exchange chromatography, an ionic strength of the eluent is different from that of ordinary eluents. The result is that because the separation conditions are changed, measurement can become difficult, or it is necessary to make changes in the measurement conditions. Furthermore, because the optimum pH for the formation of the complex mentioned above is about 4.5–6.5, and preferably 5.0–6.0, there is a danger that the Hb will be denaturated.

As another method for the elimination of L-HbA$_{1c}$, there is a method in which the blood sample is diluted, thereby lowering the glucose concentration, resulting in an acceleration of elimination of L-HbA$_{1c}$. When this method is employed practically, for example, erythrocytes are incubated in a large excess of physiological saline, or the hemolysate is dialyzed. However, all of these processes require a long period of time, and thus they are not appropriate methods for use in clinical testing.

SUMMARY OF THE INVENTION

The eliminating agent of this invention used for the measurement of the amount of glycosylated hemoglobins in a blood sample, which overcomes the above-discussed and other numerous disadvantages and deficiencies of the prior art, comprises condensed phosphoric acids and/or the salts thereof as the main ingredient, wherein said agent eliminates labile glycosylated hemoglobin $A_{1c}$ into non-glycosylated hemoglobin and glucose.

The method for measuring glycosylated hemoglobins of this invention comprises the steps of: admixing a blood sample containing at least erythrocytes and/or glycosylated hemoglobins with an eliminating reagent containing the above-mentioned eliminating agent, so that labile glycosylated hemoglobin $A_{1c}$, which is contained in said erythrocytes and/or present in liberated form, is eliminated into non-glycosylated hemoglobin and glucose; treating the blood sample processed in this way by ion-exchange chromatography, so that non-glycosylated hemoglobins and various types of glycosylated hemoglobins in the sample are separated from each other; and measuring the amount of stable glycosylated hemoglobin $A_{1c}$.

The reagent used for the measurement of the amount of glycosylated hemoglobins in a blood sample of this invention comprises the above-mentioned eliminating agent and hemolysis agent.

The eluent of this invention is used for the separation of glycosylated hemoglobins in a blood sample by ion-exchange chromatography to measure the amount of the said glycosylated hemoglobins, and comprises the above-mentioned eliminating agent.

Thus, the invention described herein makes possible the objectives of (1) providing an eliminating agent that can eliminate only labile hemoglobin $A_{1c}$ from hemoglobin $A_{1c}$ in a blood sample, so that stable hemoglobin $A_{1c}$ can be measured accurately in a short period of time without denaturating the hemoglobins; (2) providing a method for measuring glycosylated hemoglobins using the said eliminating agent; (3) providing a reagent for measuring glycosylated hemoglobins that comprises the eliminating agent mentioned above and a hemolysis agent, and with which the S-$HbA_{1c}$ level in the blood sample is measured accurately; (4) providing an eluent for the measurement of glycosylated hemoglobins that contains the eliminating agent mentioned above, and with which the S-$HbA_{1c}$ level in the blood is measured effectively by the use of a column chromatography, and (5) providing a method for measurement of S-$HbA_{1c}$ as an index of medical treatment for diabetes mellitus in which the transitory increases and decreases in blood glucose do not have an effect upon the measured values.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

The condensed phosphoric acids and/or the salts thereof that are the main ingredients of the eliminating agent of this invention have the property of eliminating glycosylated hemoglobins, especially labile $HbA_{1c}$, in the blood. The condensed phosphoric acids include metaphosphoric acids that are represented by the formula $(HPO_3)_n$, in which n is an integer of 2 or more, polyphosphoric acids that have P-O-P bonds and contain 2 atoms or more of phosphorus, and their analogues. The metaphosphoric acids include trimetaphosphoric acid (III), tetrametaphosphoric acid (IV), etc.; and the polyphosphoric acid includes pyrophosphoric acid (V), tetrapolyphosphoric acid (VI), etc.

(III)

(IV)

(V)

(VI)

As related analogues, there are the compounds that have side chains added to the above formulae, compounds that are further condensed, and the like. For example, there are the compounds having the formulae shown below as VII, VIII, and IX.

(VII)

-continued

In addition to the compounds mentioned above, compounds that form the condensed phosphoric acids when dissolved in water are included. For example, it is possible to use phosphorus pentaoxide in this invention. By the hydrolysis of phosphorus pentaoxide upon its being dissolved in water, ultrapolyphosphoric acid (IX), tetrametaphosphoric acid (IV), tetrapolyphosphoric acid (VI), etc., are formed. However, orthophosphoric acid, the final product of hydrolysis, does not have this property.

The most preferable degree of condensation for the condensed phosphoric acids mentioned above, from the point of view of effective elimination of L-HbA$_{1c}$, is 2 to 6. However, compounds in which the degree of condensation is greater than 6 can be used because the compounds will be hydrolyzed to form the condensed phosphoric acids with 2 to 6 phosphorus atoms in an aqueous solution.

The salts of these condensed phosphoric acids can be used to give the same effects as when the condensed phosphoric acids themselves are used. The kind of the salts is not restricted. For example, salts of alkaline metals and alkali earth metals can be used, and Na salts, K salts, and the like are particularly preferable.

The amount of the eliminating agent for L-HbA$_{1c}$ that is to be used depends on the kind of compound used, the conditions at the time of measurement (for example, conditions of pretreatment such as the hemolysis of the blood, temperature, time of incubation, pH of the solvent used, etc.). However, in general, per milliliter of whole blood, the amount used will be 1–6000 mg. For example, to a sample solution containing 3 μl of whole blood that has been hemolyzed with 450 μl of a solution of the hemolysis agent, pyrophosphoric acid is added so that the final concentration is about 0.1–4.0 W/V %, and preferably, 0.5–2.0 W/V %. When tetrapolyphosphoric acid is used, the final concentration is about 0.001–1.0 W/V %, and preferably 0.01–0.2 W/V %. When the eluent used for column chromatography contains the above-mentioned eliminating agent, and when the eliminating agent is tetrapolyphosphoric acid, the concentration of the eliminating agent is in the range of 0.001 to 1 W/V %. When the eliminating agent is pyrophosphoric acid, the concentration is in the range of about 0.1 to 5 W/V %. When the amount of eliminating agent is too small, the elimination of the L-HbA$_{1c}$ will not be effective, and when the amount of eliminating agent is too great, separation of Hb components by column chromatography will become difficult.

When the eluent for column chromatography that contains the above-mentioned eliminating agent is used, the longer the time of contact between the Hb and the condensed phosphoric acids in the eluent is, that is, the longer the elution time is, the more effective is the elimination of L-HbA$_{1c}$. Therefore, when the elution time is long, the amount of condensed phosphoric acids and/or the salts thereof in the eluent can be decreased, and when the elution time is to be short, the amount must be increased compared to when the elution time is long.

Because Hb is contained in the erythrocytes, when the amount of Hb in the blood is to be measured, the blood is generally hemolyzed in advance. A reagent containing both the eliminating agent mentioned above and a hemolysis agent can also be used conveniently. As the hemolysis agent, surfactants are preferably used. As hemolysis agents, higher fatty alcohols, alkylarylpolyether alcohols, polyoxyethylene ether of sulfonates, polyoxyethylene ether of sulfates, and polyoxyethylene adducts of fatty esters of sorbitol can be used. The amount of hemolysis agent to be used depends on the kind of agent that is used and on other factors, but in general, 10–2000 mg is used per milliliter of blood. For example, 1 ml of blood can be hemolyzed by adding 2–400 ml of treatment liquid for hemolysis in which a hemolysis agent is contained in the concentration of 0.01–2 vol %, and by shaking the mixture. If there is an excessive amount of hemolysis agent, it is difficult to separate hemoglobins by chromatography. Preservatives such as, for example, sodium azide, can be added in the concentration of 0.005–0.1 W/V % to the reagent that contains both the eliminating agent mentioned above and a hemolysis agent, or to the eluent containing the eliminating agent. The reagent or eluent containing the preservatives can be stored for relatively long periods of time.

As a packing material for chromatography for the separation of the different kinds of glycosylated hemoglobins and other kinds of hemoglobins from each other, cation-exchange resins can be used. There is no particular limitation on the kind of cation-exchange resin that can be used. For example, particles of copolymers made of methacrylic acid and methacrylates or copolymers made of methacrylic acid and divinylbenzene can be used. It is also possible to use silica particles that have been coated with (meth)acrylic polymers. It is possible to use such buffers as phosphate buffer, citrate-Na$_2$HPO$_4$ buffer, sodium citrate-NaOH buffer, acidic potassium phthalate-NaOH buffer, etc., as the liquid used for chromatography. Generally, phosphate buffer is used. The ion concentration of the phosphate should be within the limits of 10–400 mM.

For the measurement of the glycosylated hemoglobins by means of this invention, first of all, for example, a blood sample is pretreated with a hemolysis agent when necessary, to hemolyze it. This pretreated sample that contains erythrocytes and/or Hb is mixed with the medium for elimination that contains the eliminating agent mentioned above. Alternatively, a reagent containing the eliminating agent and the hemolysis agent is prepared in advance, and the blood sample is mixed with this reagent, so that the hemolysis and the elimination of L-HbA$_{1c}$ take place in a single step. The more acidic the mixture of the sample and the solution of eliminating agent is, the faster the elimination of the L-HbA$_{1c}$. However, when the pH of the mixture is too low, the Hb may be denatured. Also, it is difficult to separate out Hbs by chromatography at very high or very low pH. Accordingly, the pH of the mixture containing a sample and an eliminating agent is generally adjusted so as to be from 4.6 to 7.0, and preferably, from pH 5.3 to pH 6.5. For example, a 0.001–0.01 M phosphate buffer that contains an eliminating agent and a hemolysis agent is prepared, and the pH of the buffer is adjusted in the appropriate range. The time needed for the incubation of sample with the eliminating agent varies depending on the kind of eliminating agent, its concentration, the pH, and other conditions, but in general, it is 10 minutes or more at room temperature, and preferably 10 to 30 minutes. By the raising of the temperature, it is possible to shorten the incubation time. For example, it is possible to incubate the mixture for about 3–7 minutes at 37° C., and for about 1–3 minutes at 50° C. A sample treated in this way is put on an ion-exchange chromatography column (for example, high-performance liquid chromatography can be used), and the different kinds of Hbs can be separated.

A method other than the above that can be recommended involves the preparation of a buffer that contains an eliminating agent, and its use as an eluent in the chromatography of the sample of hemolyzed blood. By this method, the elimination of the L-HbA$_{1c}$ and the separation of the various kinds of hemoglobins in the sample occur in a single step. With this kind of method, the main ingredients of the eliminating agent (i.e., a condensed phosphoric acid and/or the salt thereof) also act as a buffer in the eluent. Also, condensed phosphoric acids and their salts can block heavy-metal ions from causing undesirable effects on separation during the process of ion-exchange chromatography. The pH of this kind of an eluent can be 4.6–7.5, and preferably, 5.0–7.0. The time for contact of the sample with the eluent needed to eliminate the L-HbA$_{1c}$ depends on the kind of condensed phosphoric acid used, its concentration, the pH, the temperature inside the column, etc., but in general, 1 minute or more is needed. Generally, the temperature inside the column is selected so as to be from room temperature to about 45° C.

The elimination of L-HbA$_{1c}$ occurs at different steps depending on the column treatment. The following situations are possible.

(1) In an automated assay system by high-performance liquid chromatography or the like, elimination occurs during the contact of the blood sample with the eluent in a tube before the sample enters the column.

(2) In the afore-mentioned tube, some of the L-HbA$_{1c}$ is eliminated, and the remainder enters the column as L-HbA$_{1c}$. After the L-HbA$_{1c}$ is absorbed to the packing material (i.e., the adsorbent), the L-HbA$_{1c}$ eliminates when it is released from the adsorbent and/or eluted by the eluent.

(3) After the L-HbA$_{1c}$ has been adsorbed to the absorbent, it is liberated and eliminated by the eluent.

Situations 1 and 2 above can be the case in which a high-performance liquid chromatography is employed, and situation 3 can be the case in which open types of column chromatography (for example, with a small column) is employed and the injection step of the sample and the elution step are carried out separately.

It is possible that after the blood sample is treated with the eliminating agent, the sample is eluted by use of the eluent that contains the eliminating agent, and in this case, the L-HbA$_{1c}$ is eliminated with particular effectiveness.

As mentioned above, the sample can be put on a column after being treated by the step of elimination. The sample can also be treated by a step that involves elimination and elution in a column by use of an eluent containing the eliminating agent. In both cases, the eluate from the column contains almost no L-HbA$_{1c}$. The reason is that L-HbA$_{1c}$ has been eliminated into glucose and hemoglobin effectively by the eliminating agent.

By the measurement of the absorbance of the fractions eluted from the column by means of dual-wavelength colorimetry or the like at, for example, 415 nm for the primary wavelength and 500 nm for the reference wavelength, it is possible to measure the amount of S-HbA$_{1c}$ in the sample accurately.

The elimination of the L-HbA$_{1c}$ by the use of the eliminating agent of this invention may be due to the 2,3-DPG pocket in Hb. The 2,3-DPG pocket has been reported in detail by Benesch et al., *Biochem. Biophys. Res. Commun.*, 26, 162, (1967); and by Chanutin et al., *Arch. Biochem. Biophys*, 121:96, (1967); etc. This 2,3-DPG pocket is composed of basic amino acid residues such as histidine, lysine, etc., in the β-chain of the Hb, and of the N-terminal valine in the βchain of HbA$_{1c}$. The 2,3-DPG pocket is cationic. Because the condensed phosphoric acids or the salts thereof used in this invention are anionic, they have strong affinity for the 2,3-DPG pocket. The molecular configuration of the condensed phosphoric acid or the salt thereof is also suitable for binding to the 2,3-DPG pocket. For that reason, it binds competitively with glucose onto the end of the β-chain of Hb. The result is that the elimination of L-HbA$_{1c}$ is accelerated.

In this way, by the elimination of L-HbA$_{1c}$ by the use of condensed phosphoric acids and/or the salts thereof, L-HbA$_{1c}$ is eliminated from the sample, and only S-HbA$_{1c}$ remains in the sample. This eliminating agent has no effect on the elution pattern of Hb components by the use of ion-exchange chromatography. For that reason, the S-HbA$_{1c}$ can be separated by the use of the same methods that are used conventionally, that is, by ion-exchange chromatography, and the amount of S-HbA$_{1c}$ can be measured with accuracy.

EXAMPLES

This invention will be explained with reference to the following examples.

Measurement Methods

Figure 1:
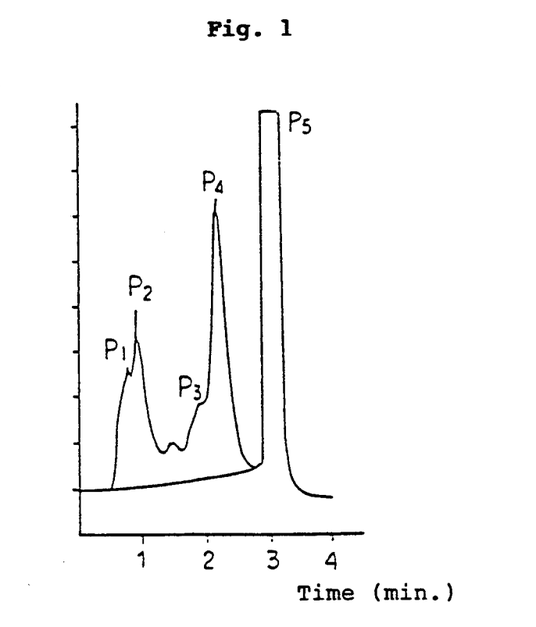
FIG. 1 is a chart that shows the elution pattern of Hb components in a blood sample that has been treated and separated by means of ion-exchange chromatography according to this invention.

In the following examples, the amount of HbA$_{1c}$ was measured by the use of a Hi-Auto A$_{1c}$ HA-8120 analyzer from Kyoto Daiichi Kagaku Co., Ltd. Measurement was done under appropriate conditions. This model HA-8120 is an apparatus designed for the assay of HbA$_1$ and HbA$_{1c}$ by the use of HPLC, and its column is packed with about 2 g of fine particles of a copolymer made of methacrylic acid and methacrylates as a cation-exchange resin. Various kinds of Hbs can be separated in 4 minutes by cation-exchange and eluted. A typical elution pattern of Hbs obtained by the use of this apparatus is shown in FIG. 1. In FIG. 1, P$_1$ and P$_2$ are peaks that arise from HbA$_{1a}$ and HbA$_{1b}$, respectively, and P$_3$ and P$_4$ are peaks that arise from L-HbA$_{1c}$ and S-HbA$_{1c}$, respectively. P$_5$ arises from another kind of hemoglobin (abbreviated HbA$_0$ below). The proportion of S-HbA$_{1c}$ that is present can be calculated from the ratio of the area of $P_4$ to the total area of all peaks. By the conventional method, because peaks $P_3$ and $P_4$ overlap, it is difficult to calculate the area of peak $P_4$ alone. However, the area of the peak $P_3$ that is obtained by the method of this invention is relatively small, and for that reason, it is possible to use the total area of the peaks $P_3$ and $P_4$ as an index of the amount of S-HbA$_{1c}$. Ordinarily, in clinical tests and the like, the amount of HbA$_{1c}$ is expressed as the total of S- and L-forms. This HbA$_{1c}$ is calculated by the use of the following equation.

$$HbA_{1c}(\%) = \frac{\text{Areas of peaks } P_3 + P_4}{\text{Total area of the } Hb \text{ peaks}} \times 100$$
$$P_1 + P_2 + P_3 + P_4 + P_5$$

Eluent A and B for use with the apparatus mentioned above (Sekisui Kagaku Kogyo Kabushiki Kaisha) were used as the eluents for the measurement of the blank value mentioned below (which value corresponds to the actual amount of HbA$_{1c}$ in the sample) and for the measurement of the reference value mentioned below (which corresponds to the actual amount of S-HbA$_{1c}$ in the sample). Both of these eluents are phosphate buffers, and their compositions were as follows.

| Eluent A | | Eluent B | |
| --- | --- | --- | --- |
| KH$_2$PO$_4$ | 9.4 g/l | KH$_2$PO$_4$ | 11 g/l |
| K$_2$HPO$_4$ | 2.5 g/l | K$_2$HPO$_4$ | 42 g/l |

Eluent A was used as the buffer to equilibrate the packing material and to separate the HbA$_{1a}$, HbA$_{1b}$, S-HbA$_{1c}$, and L-HbA$_{1c}$ by elution. Eluent B was used to elute the HbA$_0$. Switching operations are made to supply Eluent A or Eluent B to the column during the measurement.

In the following examples, the eluents used were similar to Eluent A and Eluent B, and the pH of the eluents was adjusted by changes in the concentrations of KH$_2$PO$_4$ and K$_2$HPO$_4$ in these eluents. The ion concentration was adjusted so that the retention time of the peak of HbA$_{1c}$ at the time of chromatography and the retention time of the peak of HbA$_{1c}$ when the above Eluent A and B were used would be the same. Such an eluent adjusted in this way was used in place of Eluent A for use with this apparatus, and measurements were made. The internal temperature of the column was 40° C., and the flow rate of the eluent was about 2.2 ml/min.

Measurements of Blank Values and Reference Values

A solution of hemolysis agent was prepared by the addition of 0.1 ml of Triton X-100 (Wako Pure Chemical Industries, Ltd.) as a hemolysis agent into 100 ml of a 0.005 M phosphate buffer (pH 6.3). Then, to 450 μl of this solution, 3 μl of fresh blood was added, and HbA$_{1c}$ (including both the L- and S-forms) was measured by the method described above. It was found that 5.0% of the total Hb was HbA$_{1c}$. This value was used as the blank value.

Next, about 5 ml of blood cells obtained by the centrifugation of 10 ml of fresh blood was placed in a 8/32-inch cellophane tube (Wako Pure Chemical Industries, Ltd.), and this tube was incubated in 1 liter of physiological saline two times for a total of 5 hours at 37° C. After the L-HbA$_{1c}$ was eliminated in this way, about 1.5 μl of this preparation was sampled and hemolyzed by the use of 450 μl of the solution of the hemolysis agent described above. Then the amount of HbA$_{1c}$ in this sample was measured by the same method as before, and found to be 4.3%. This value corresponds to the amount of S-HbA$_{1c}$ in the blood. The value was used as the reference value.

EXAMPLE 1

In 100 ml of 0.005 M phosphate buffer, 0.1 ml of Triton X-100 (Wako Pure Chemical Industries, Ltd.) as a hemolysis agent and about 0.1 g of tetrapolyphosphoric acid (Wako Pure Chemical Industries, Ltd.) as the eliminating agent were added and dissolved, and the pH was adjusted to 6.3 by the addition of a base. Then, to 450 μl of this reagent, 3 μl of fresh blood was added, and the mixture was allowed to stand at room temperature for 10 minutes, resulting in the hemolysis of blood and elimination of L-HbA$_{1c}$. The amount of HbA$_{1c}$ in this sample was measured and found to be 4.4%. Separately, a solution of a hemolysis agent that did not contain tetrapolyphosphoric acid (i.e., the dissoluting agent) was prepared, and the HbA$_{1c}$ was measured by the same method.

Figure 2:
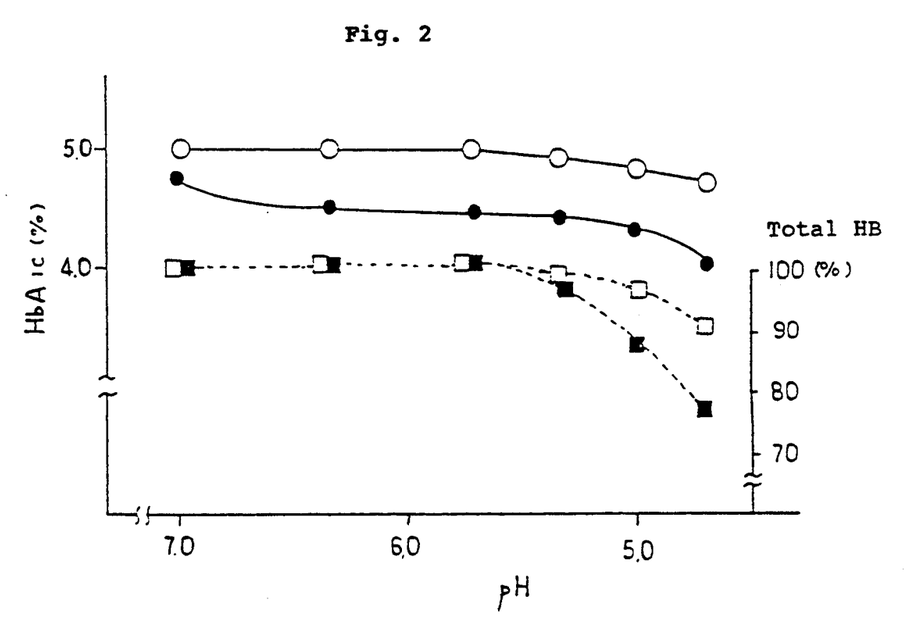
FIG. 2 is of graphs showing the relationships of the pH, the amount of $HbA_{1c}$, and the total amount of Hb obtained when a blood sample is treated with medium that contains the eliminating agent of this invention and medium that does not contain the eliminating agent.

Next, various eliminating reagents containing the eliminating agent and the hemolysis agent, and various solutions of the hemolysis agent (which did not contain the eliminating agent), the pH values of which were set at 7.0, 6.3, 5.8, 5.3, 5.0, and 4.6, respectively, were prepared, and HbA$_{1c}$ was measured in the same way using these reagents and solutions of the hemolysis agent. The amounts of HbA$_{1c}$ compared to the total Hb are shown in FIG. 2 by the solid lines (closed circles indicate the values obtained when the reagent that contained both eliminating agent and hemolysis agent was used; and open circles indicate the values obtained when the solution that contained only the hemolysis agent was used). The amounts of total Hb are shown in FIG. 2 by the dotted lines (closed squares indicate the values obtained when the liquid agent that contained both eliminating agent and hemolysis agent was used; and open squares indicate the values obtained when the solution that contained only the hemolysis agent was used). The total Hb level was calculated in terms of the percentage of the total Hb level in the original sample, which was taken to be 100%.

FIG. 2 shows that the HbA$_{1c}$ level decreases as the pH decreases, which shows that L-HbA$_{1c}$ was eliminated. However, when the pH dropped below 5.3, the elimination of heme was shown by loss of color, and the total Hb level was seen to decrease. In particular, when an eliminating agent of this invention incorporates tetrapolyphosphoric acid, this tendency is marked, and the total amount of Hb at pH 4.6 was about 75% that at pH 6.3. When measurements are done with the use of the eliminating agent of this invention, it is clearly possible to cause the elimination of L-HbA$_{1c}$ in the pH range of 7.0 to 5.3 without causing changes in the Hb.

Next, an eliminating reagent preservative was prepared by the addition of 0.01 g of sodium azide as a preservative to the liquid agent that contained Triton X-100 and tetrapolyphosphoric acid mentioned above. This liquid agent was stored at room temperature for one month, and used in the same way as before in the measurement of HbA$_{1c}$. Substantially the same results were obtained as when measurements were done immediately after preparation.

EXAMPLE 2

A solution of hemolysis agent was prepared by the methods used in Example 1 that contained only a hemolysis agent and did not contain tetrapolyphosphoric acid. To this, 3 μl of fresh blood was added for hemolysis. The hemolyzed mixture obtained was treated by column chromatography by use of an eluent that contained the eliminating agent of this invention, and the amounts of $HbA_{1c}$ and total Hb were measured. The eluent used was a buffer with 65 mM $KH_2PO_4$ and 15 mM $K_2HPO_4$, and contained sodium tetrapolyphosphate in the concentration of 0.2 W/V %. The pH of the eluent was 4.6. Separately, eluents having the same composition and having different pH were prepared, the pH of which was 5.5, 6.5, and 7.5, respectively. The amounts of $HbA_{1c}$ and total hb were measured, respectively, using these eluents. The ionic concentration and pH of the eluent, the amount of $HbA_{1c}$, and the total amount of Hb are shown in Table 1.

TABLE 1

| pH of eluent | 4.6 | 5.5 | 6.5 | 7.5 |
|---|---|---|---|---|
| Ionic concentration of eluent (mM) | 90 | 85 | 75 | 70 |
| $HbA_{1c}$ (%) | 4.3 | 4.3 | 4.4 | 4.6 |
| Total Hb (%) | 82 | 96 | 100 | 100 |

The trends seen in Table 1 are similar to those seen in Example 1. That is, the lower the pH of the eluent used, the lower the amount of $HbA_{1c}$ (which shows that $HbA_{1c}$ had been eliminated); also, it can be seen that the lower the pH of the eluent used, the lower the value for total Hb, because of the elimination of heme.

EXAMPLE 3

Eliminating reagents containing the eliminating agent and the hemolysis agent (all with a pH of about 6.0) were prepared as in Example 1, except that the amounts of tetrapolyphosphoric acid were 0.001 g, 0.005 g, 0.05 g, 0.2 g, or 1.0 g. With the use of these reagents and the methods used in Example 1, the amount of $HbA_{1c}$ was measured. The results are shown in Table 2.

TABLE 2

| | Concentration of tetrapolyphosphoric acid (%) | | | | |
|---|---|---|---|---|---|
| | 0.001 | 0.005 | 0.05 | 0.2 | 1.0 |
| Amount of $HbA_{1c}$ (%) | 4.7 | 4.5 | 4.4 | 4.4 | 4.3 |

Table 2 shows that even at the relatively low concentration of 0.005% tetrapolyphosphoric acid, L-$HbA_{1c}$ was efficiently eliminated. When the concentration of tetrapolyphosphoric acid was 1.0%, the pattern obtained by chromatography was broadened. Therefore, a relatively low concentration is preferable.

EXAMPLE 4

Eluents were prepared by the addition of sodium tetrapolyphosphate (Nacalai Tesque, Inc.) to buffers (pH 6.1) that contained 65 mM $KH_2PO_4$ and 15 mM $K_2HPO_4$ to the final concentrations of 0.005, 0.02, 0.2, and 0.5 W/V %, respectively. A sample was hemolyzed in the same way as in Example 2, chromatographed by the use of the above eluents, and measured for the level of $HbA_{1c}$. The results are shown in Table 3.

TABLE 3

| Sodium tetrapolyphosphate (W/V %) | 0.005 | 0.02 | 0.2 | 0.5 |
|---|---|---|---|---|
| Amount of $HbA_{1c}$ (%) | 4.7 | 4.4 | 4.3 | 4.3 |

Table 3 shows that even at the relatively low concentration of 0.005% tetrapolyphosphoric acid, L-$HbA_{1c}$ was efficiently eliminated.

Next, to the above eluent with the sodium tetrapolyphosphate concentration of 0.2 W/V %, sodium azide was added to the concentration of 0.01 W/V % as a preservative, and the mixture was stored at room temperature for 1 month. L-$HbA_{1c}$ was measured in the same way as above with the use of this eluent, and substantially the same results were obtained.

EXAMPLE 5

An eliminating reagent containing the eliminating agent and the hemolysis agent with a pH of 6.0 was prepared as in Example 1. This was mixed with a blood sample and kept for predetermined lengths of time at 37° C., 50° C., or 60° C., after this incubation, it was used in the measurement of $HbA_{1c}$. The results are shown in FIG. 3.

Figure 3:
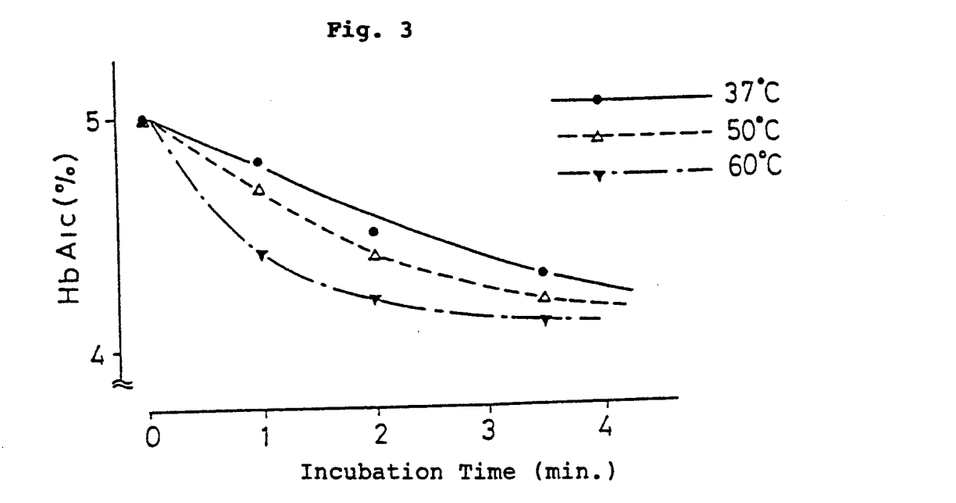
FIG. 3 is of a graph showing the relationship between the time that a blood sample is treated and the total amount of $HbA_{1c}$ when the sample is treated according to this invention at various temperatures.

FIG. 3 shows that L-$HbA_{1c}$ is eliminated more rapidly as the reaction temperature is raised. However, when incubation was at 60° C. for 3.5 minutes, there was some decomposition of Hb, and the total Hb level decreased to about 90% of the original level. For this reason, incubation for long periods of time at high temperatures is not recommended.

EXAMPLE 6

Figure 4A:
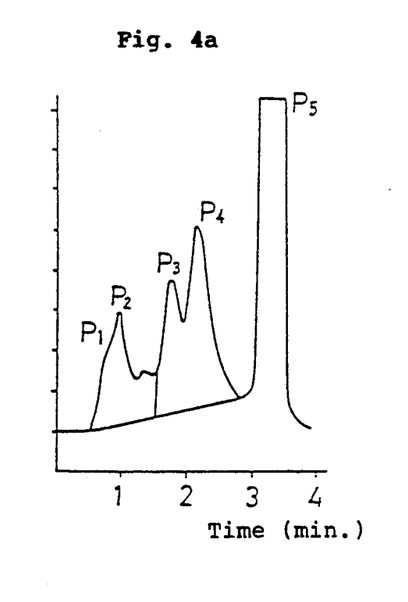
FIGS. 4a and 4b are charts that show the elution patterns obtained by ion-exchange chromatography when a blood sample has a high level of L-$HbA_{1c}$ and when the said sample has been treated by the method of this invention, respectively.
Figure 4B:
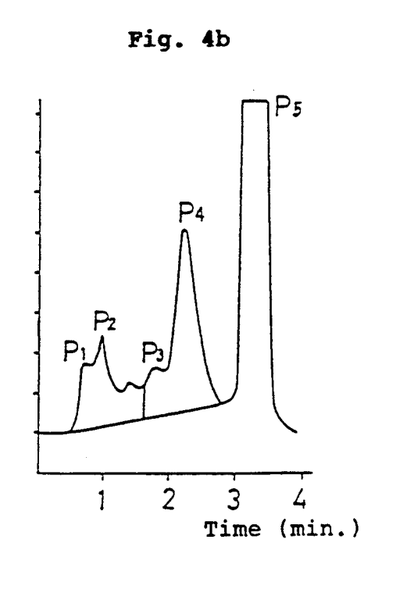

About 5 ml of erythrocytes obtained by the centrifugation of 10 ml of fresh blood was put into a 8/32-inch cellophane tube (Wako Pure Chemical Industries, Ltd.) and dialyzed for 5 hours against 1000 ml of an isotonic solution of D-glucose (1000 mg/dl) at 37° C. This resulted in a sample with a high level of L-$HbA_{1c}$. A solution of hemolysis agent that did not contain an eliminating agent was prepared that had a pH of 6.0 by the methods used in Example 1. To 450 μl of this solution of a hemolysis agent, about 1.5 μl of the above sample was added and hemolyzed. The amount of $HbA_{1c}$ in the hemolysate was 6.0%. The elution pattern obtained by chromatography of this sample is shown in FIG. 4a. Next, an eliminating reagent was prepared by the addition of tetrapolyphosphoric acid to the concentration of 0.1% to the above solution of hemolysis agent, and by the same methods as above, a sample that contained a high concentration of L-$HbA_{1c}$ was added. After the mixture was incubated at 50° C. for two minutes, its $HbA_{1c}$ level was measured and found to be 4.4%. The elution pattern obtained by chromatography of this sample is shown in FIG. 4b. The peak $P_3$ observed in FIG. 4a has almost disappeared in FIG. 4b. As shown by this example, it is possible to eliminate L-$HbA_{1c}$ satisfactorily by the use of the eliminating agent of this invention even from samples that contain high levels of L-$HbA_{1c}$.

EXAMPLE 7

Preparation and methods were the same as in Example 6, except for the use of an eliminating reagent that contained a hemolysis agent and that had 1.0% sodium pyrophosphate (Nacalai Tesque, Inc.) instead of 0.1% tetrapolyphosphoric acid. The amount of $HbA_{1c}$ was 4.5%.

EXAMPLE 8

An eluent (pH 6.1) was prepared by the methods of Example 2 that contained either sodium pyrophosphate (Wako Pure Chemical Industries, Ltd.) at the concentration of about 1.0 W/V % or ultra-polyphosphoric acid (Taihei Kagaku Co., Ltd.) at the concentration of about 0.2 W/V % instead of sodium tetrapolyphosphate. These eluents were used as in Example 2 to measure the amount of $HbA_{1c}$. The amount of $HbA_{1c}$ was 4.4% when the eluent containing sodium tetrapolyphosphate was used, and 4.3% when the eluent containing ultrapolyphosphoric acid was used.

EXAMPLE 9

By the methods of Example 1, the following eliminating reagents containing an eliminating agent and a hemolysis agent were prepared: an eliminating reagent (pH 6.0) containing sodium pyrophosphate at the concentration of about 2.0% instead of tetrapolyphosphoric acid; an eliminating reagent (pH 6.0) containing ultrapolyphosphoric acid (Taihei Kagaku Co., Ltd.) at the concentration of about 0.1% instead of tetrapolyphosphoric acid; and an eliminating reagent (pH 6.0) containing sodium hexametaphosphate at the concentration of about 1.1% instead of tetrapolyphosphoric acid. These were used in the same way as in Example 1 and the amount of $HbA_{1c}$ was measured and found be 4.5%, 4.4%, and 4.4%, respectively, with these three eliminating reagents.

Separately, eliminating reagents that contained a preservative was prepared in the same way as in Example 1 and stored for 7 days at room temperature. When this was used by the same methods for measurement, essentially the same results were obtained.

EXAMPLE 10

To the Eluent A made of phosphate buffer (Sekisui Kagaku Kogyo Kabushiki Kaisha) for use in the measurement of $HbA_1$, tetrapolyphosphoric acid was added to give the concentration of 0.005%, by which an eluent that contained an eliminating agent was obtained. Separately, a solution of hemolysis agent that did not contain an eliminating agent was prepared as in Example 1. This solution was used to hemolyze fresh blood by the methods used in Example 1. The sample obtained was immediately chromatographed with the above eluent, for separation and measurement. The elution pattern obtained was almost the same as when the eliminating reagent of Example 1 was used, and the amount of $HbA_{1c}$ was 4.4%. This showed that when an eluent that contained the eliminating agent of this invention was used, elimination of $L-HbA_{1c}$ was satisfactory.

Comparative Example 1

A solution (pH 6.0) was prepared that contained the hemolysis agent of Example 1 and sodium dihydrogen phosphate (Wako Pure Chemical Industries, Ltd.) at the concentration of about 2.0% instead of the tetrapolyphosphoric acid of Example 1. This solution was added to fresh blood, and the mixture was incubated at 50° C. for 2 minutes. The level of $HbA_{1c}$ was then measured as in Example 1, and found to be 5.0%, showing that elimination of $L-HbA_{1c}$ was not satisfactory.

Comparative Example 2

An eluent (pH 6.1) was prepared that contained boric acid (Wako Pure Chemical Industries, Ltd.) at the concentration of about 1.0 W/V % instead of the sodium tetrapolyphosphate of Example 2. The amount of $HbA_{1c}$ was measured by the methods of Example 2, and found to be 4.7%. Also, such an eluent was prepared so as to have the pH of 5.0; the amount of $HbA_{1c}$ was measured by the same methods, and found to be 4.4%. However, the peaks of Hb were broad, and the total Hb had decreased to about 80% compared to the original level. These findings showed that it is necessary to lower the pH more when boric acid is used to eliminate $L-HbA_{1c}$ than when sodium tetrapolyphosphate is used, and that for that reason, decomposition of Hb increases.

Comparative Example 3

A reagent for the elimination of $L-HbA_{1c}$ that contained the same hemolysis agent as in Example 1 (at the same concentration as in Example 1), 0.01 M semicarbazide hydrochloride (Wako Pure Chemical Industries, Ltd.), and 0.004 M aniline (Wako Pure Chemical Industries, Ltd.). This was used to hemolyze fresh blood as in Example 1, and the hemolyzate was incubated for 2 minutes at 60° C. The $HbA_{1c}$ was measured and found to be 4.6%. However, the fractionation pattern was considerably broadened, and the total area of the Hb peaks was about 70% of the original level.

Comparative Example 4

An eluent (pH 6.1) was prepared that contained 5 mM semicarbazide hydrochloride (Wako Pure Chemical Industries, Ltd.) and 2 mM aniline (Wako Pure Chemical Industries, Ltd.) instead of sodium tetrapolyphosphate. This was used in the same way as in Example 2 to measure $HbA_{1c}$, which was found to be 4.5 W/V %. However, the elution pattern for Hb was broadened, and the total amount of Hb was 80% compared to the original level.

Comparative Example 5

An eliminating reagent was prepared that contained the same hemolysis agent as in Example 1 (at the same concentration as in Example 1) and 1% boric acid in 0.005 M phosphate buffer, pH 5.3. This was used to hemolyze fresh blood in the same way as in Example 1, and the hemolyzate was incubated for 2 minutes at 50° C. The amount of $HbA_{1c}$ in the hemolyzate after incubation was measured, and found to be 4.4%. However, when measurements were made in the case of boric acid at the concentration of 0.1% and a pH of 6.0, the amount of $HbA_{1c}$ was 4.8%. This finding showed that it was not possible to eliminate $L-HbA_{1c}$ satisfactorily when the concentration of boric acid was low.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method of analyzing a blood sample containing labile glycosylated hemoglobin $A_{1c}$ and stable glycosylated hemoglobin $A_{1c}$ comprising
   admixing a blood sample containing labile glycosylated hemoglobin $A_{1c}$ with an eliminating agent selected from the group consisting of condensed phosphoric acids and salts thereof;
   allowing the blood sample and eliminating agent to remain in contact with each other for a sufficient period of time so that the eliminating agent converts the labile glycosylated hemoglobin $A_{1c}$ into non-glycosylated hemoglobin and glucose to form a treated sample; and analyzing said treated sample to determine the amount of stable glycosylated hemoglobin $A_{1c}$.

2. The method as claimed in claim 1, wherein the eliminating agent is combined with the blood sample in an amount sufficient to convert substantially all of the labile glycosylated hemoglobin $A_{1c}$ in the blood sample to non-glycosylated hemoglobin and glucose.

3. The method as claimed in claim 1, wherein the eliminating agent is selected from the group consisting of metaphosphoric acid, polyphosphoric acid, analogs thereof, and mixtures thereof.

4. The method as claimed in claim 1, further comprising:
   combining a surfactant with the admixed blood and eliminating agent wherein the surfactant acts as a hemolysis agent.

5. The method as claimed in claim 4, wherein the eliminating agent is selected from the group consisting of metaphosphoric acid, polyphosphoric acid, analogs thereof and mixtures thereof.

6. A method of treating blood sample comprising:
   combining a blood sample containing labile glycosylated hemoglobin $A_{1c}$, stable glycosylated hemoglobin $A_{1c}$, and hemoglobins other than the labile glycosylated hemoglobin $A_{1c}$ and the stable glycosylated hemoglobin $A_{1c}$ with a buffer solution containing a hemolysis agent to create a hemolyzed mixture;
   subjecting the hemolyzed mixture to ion-exchange chromatography by using an eluent which comprises condensed phosphoric acids and/or salts thereof in a manner so as to eliminate the labile glycosylated hemoglobin $A_{1c}$ from the hemolyzed mixture and to separate the stable glycosylated hemoglobin $A_{1c}$ from the other hemoglobins in the blood sample.

7. The method as claimed in claim 6, further comprising:
   measuring the amount of stable glycosylated hemoglobin $A_{1c}$.

8. The method as claimed in claim 6, further comprising:
   measuring the amount of glycosylated hemoglobin components that are obtained by eliminating the labile glycosylated hemoglobin $A_{1c}$.

9. The method as claimed in claim 6, wherein the eluent is a solution containing at least one compound which is selected from the group consisting of metaphosphoric acid, polyphosphoric acid, analogs thereof, and mixtures thereof.

10. The method as claimed in claim 6, wherein the eluent has a pH in the range of from about 4.6 to about 7.0.

11. A method of analyzing a blood sample using condensed phosphoric acids and/or salts thereof for eliminating labile glycosylated hemoglobin $A_{1c}$ component from glycosylated hemoglobin $A_1$ in said blood sample comprising:
   admixing a blood sample containing at least erythrocytes and/or glycosylated hemoglobins with the condensed phosphoric acids and/or salts thereof in order that the condensed phosphoric acids and/or salts thereof convert the labile glycosylated hemoglobin $A_{1c}$ into non-glycosylated hemoglobin and glucose; and
   analyzing said sample to determine the amount of glycosylated hemoglobin $A_1$.

12. A method according to claim 11, wherein the condensed phosphoric acids and/or salts thereof are selected from the group consisting of metaphosphoric acid, polyphosphoric acid, analogs thereof, and mixtures thereof.

13. A method of using an eluent which comprises condensed phosphoric acids and/or salts thereof for separating stable glycosylated hemoglobin $A_{1c}$ from hemoglobins other than the stable glycosylated hemoglobin $A_{1c}$ in the blood sample by ion-exchange chromatography to measure the amount of stable glycosylated hemoglobin $A_{1c}$ comprising the steps of:
   combining a blood sample containing labile glycosylated hemoglobin $A_{1c}$, stable glycosylated hemoglobin $A_{1c}$ and hemoglobins other than the labile glycosylated hemoglobin $A_{1c}$ and the stable glycosylated hemoglobin $A_{1c}$ with a buffer solution containing a hemolysis agent to create a hemolyzed mixture;
   subjecting the hemolyzed mixture to ion-exchange chromatography by using the eluent which comprises condenses phosphoric acids and/or salts thereof in a manner so as to separate the stable glycosylated hemoglobin $A_{1c}$ from other hemoglobins in the blood sample.

14. A method according to claim 13, wherein the condensed phosphoric acids and/or salts thereof are selected from the group consisting of metaphosphoric acid, polyphosphoric acid, analogs thereof, and mixtures thereof.

* * * * *

UNITED STATES PATENT AND TRADEMARK OFFICE
CERTIFICATE OF CORRECTION

PATENT NO. : 5,292,663
DATED : March 8, 1994
INVENTOR(S) : K. Yamazaki; M. Takechi; T. Kawabe; M. Yokoi It is certified that error appears in the above-indentified patent and that said Letters Patent is hereby corrected as shown below:

On the title page, item [60], under Related U.S. Application Data, "Division of Ser. No. 758,383, Sep. 3, 1991, abandoned," should be replaced with --Division of Ser. No. 758,383, Sep. 3, 1991, now issued as U.S. Patent No. 5,453,379,--.

Col. 1, line 9, "Sep. 3, 1991, now abandoned," should be replaced with --Sep. 3, 1991, now U.S. Pat. No. 5,453,379,--.

Signed and Sealed this

Sixth Day of August, 1996

Attest:

BRUCE LEHMAN

Attesting Officer

Commissioner of Patents and Trademarks